United States Patent [19]

Dodson

[11] Patent Number: 5,107,469

[45] Date of Patent: Apr. 21, 1992

[54] DIGITAL LOW-POWER PROGRAMMABLE ALARM CLOCK FOR USE WITH REFLECTANCE PHOTOMETER INSTRUMENTS AND THE LIKE

[75] Inventor: Neil A. Dodson, South Bend, Ind.

[73] Assignee: Miles Inc., Elkhart, Ind.

[21] Appl. No.: 561,338

[22] Filed: Jul. 31, 1990

[51] Int. Cl.[5] ............................. G04F 8/00; G01J 1/40
[52] U.S. Cl. ..................................... 368/109; 368/250; 356/234
[58] Field of Search ................... 368/10, 107-113, 368/250, 251; 356/234, 235; 364/569; 377/20

[56] References Cited

U.S. PATENT DOCUMENTS

| | | | |
|---|---|---|---|
| 4,684,261 | 8/1987 | Arnold et al. | 368/107 |
| 4,690,566 | 9/1987 | Robertsen | 368/108 |
| 5,012,435 | 4/1991 | Bailey et al. | 364/569 |

*Primary Examiner*—Vit W. Miska
*Attorney, Agent, or Firm*—Roger N. Coe

[57] ABSTRACT

A low-power programmable alarm clock system is provided for use with microprocessor-based reflectance photometer systems for generating an alarm control signal at pre-programmed alarm activation times. The system utilizes an alarm clock circuit which includes means for storing a count value corresponding to the number of predefined time periods existing between a given instantaneous time and a pre-programmed alarm activation time, means for generating a signal corresponding to the passage of each of said predefined time periods and using the generator signal to increment the stored count value each time the predefined time period has elapsed, and means for generating an alarm activation signal when the stored count value has been incremented to a predefined activation value. The programmable alarm clock circuit operates in conjunction with a transistor-based switching arrangement and the system microprocessor in such a way that the required count value is calculated and stored into a shift register/counter each time the reflectance photometer system is powered down and an alarm function is found to be activated. The alarm clock circuit then takes over and operates under negligible power consumption conditions and generates an alarm control signal which reactivates the overall system circuitry when the pre-programmed alarm activation time has been reached.

15 Claims, 3 Drawing Sheets

DIGITAL LOW-POWER PROGRAMMABLE ALARM CLOCK FOR USE WITH REFLECTANCE PHOTOMETER INSTRUMENTS AND THE LIKE

BACKGROUND OF THE INVENTION

1. Field of the Invention

This invention generally relates to reflectance photometer instruments for controlled administering of insulin in diabetes management. More particularly, this invention relates to an improved programmable alarm clock circuit specifically adapted for use with such instuments.

2. Description of the Prior Art

Instruments designed for accurate and convenient measurement of blood glucose levels are increasingly being used by diabetics as an integral part of in-home diabetes management programs. A variety of such instruments are commercially available for use by diabetics for monitoring and recording their blood glucose levels and adjusting insulin-administration quantities and schedules in conjunction with appropriate medical supervision.

Such reflectance photometer instruments or glucose monitors typically operate on reflectance or absorption photometry principles for providing an analysis of chemically treated strips which have been coated with blood to be analyzed. Typically, needle or lancet arrangements are provided for extracting an individual's blood. The monitoring individual then coats a chemically-treated reagent strip with the extracted blood and inserts the blood-coated strip, after a predefined reaction time period has elapsed, into the reflectance photometer instrument for photometric analysis of the blood glucose content using electronic sensing circuitry.

The more sophisticated reflectance photometer systems are portable, self-contained systems which include mechanical or electro-mechanical means for extracting blood from an individual and transferring the blood to glucose-sensitive chemical reagent means, and an electronic analysis system which operates under control of a microprocessor and includes photosensing electronics connected to a microcomputer or custom-integrated circuit for analyzing the chemical reagent means for providing an external indication of the measured glucose level. The external indication is generally in the form of a LCD display which can be used by a diabetic for instantaneous insulin-level adjustment. The reflectance photometer systems can also include a provision for maintaining a log of periodically taken glucose readings for purposes of subsequent medical study and treatment. Such microprocessor-based systems are advantageous because of their accuracy of measurement and, particularly, because they can be conveniently programmed to provide a variety of functions in addition to basic blood analysis.

One important peripheral function required of such sophisticated systems is the ability to provide preprogrammed alarm signals for alerting diabetics at predetermined time periods to the need for, inter alia, monitoring glucose levels, receiving an insulin injection, or ingesting requisite food supplements. Conventional microprocessor-based reflectance photometer systems have typically realized this function by (i) the provision of real time clock circuits or chips containing a built-in alarm clock feature or (ii) using the microprocessor itself to generate the alarm signals by powering up the processor at regular intervals and determining whether the instantaneous time corresponds to a stored alarm time.

Major disadvantages with such approaches are the need for high power consumption and the fact that the use of separate clock chips is undesirable due to added expense and bulk, particularly in the case of portable and handheld reflectance photometer instruments where both space and power are at a premium.

Accordingly, there exists a need for providing means for implementing programmable alarm clock functions in microprocessor-based reflectance photometer instruments which is conservative in terms of power requirements, which does not require separate real time clock chips with built-in alarms and external power control circuitry, and is adapted for use with the existing microprocessor circuitry in conventional programmable reflectance photometer instruments.

SUMMARY OF THE INVENTION

An important object of the present invention is to provide a simple programmable alarm clock circuit adapted for use with microprocessor-based reflectance photometer systems and the like.

A related object of this invention is to provide such a programmable alarm clock circuit which realizes low power consumption while being operated and controlled by the microprocessor arrangement with which it is used.

A further object of the present invention is to provide a programmable alarm clock circuit of the above kind which is economically implemented and is particularly suited for use with portable, hand-held reflectance photometer instruments in applications requiring multiple programmable alarm clock functions.

Briefly, in accordance with the system of this invention, the above and other objects are realized by the provision of an alarm clock system for generating an alarm control signal at a predefined alarm activation time $T_a$, the system essentially comprising means for calculating a count value corresponding to the number $T_p$ of a predetermined time period existing between a given instantaneous time T and the predefined alarm time $T_a$, means for generating a signal corresponding to the passage of each of said predetermined time periods, storage means for being loaded with and for storing the number $T_p$ and incrementing the stored number each time the predetermined time period has elapsed, and means for generating the alarm control signal when the stored number has been incremented to a predefined maximum value.

In practically implementing the system of this invention, a programmable alarm clock circuit is provided for use with a microprocessor-based reflectance photometer system, the circuit operating independently of the microprocessor in such a way that only the alarm circuit need be powered when an alarm function is required therefrom. Accordingly, when the alarm circuit is active, the rest of the microprocessor and circuitry can be totally cut off from the system power source.

The alarm circuit itself is based upon a minimum number of low-power components so that a negligible amount of power is drawn by the circuit during the time that it remains active in providing the required alarm functions. The arrangement is such that the alarm circuit need not be powered at all when no alarm function is required therefrom; accordingly, under such conditions, the complete reflectance photometer system, including the alarm clock circuit, can be cut off from the power source.

According to a preferred embodiment, the alarm circuit system is implemented in the form of a transistor-based switch which is activated either directly when a system ON/OFF switch is turn on by a user or when, under an alarm function mode, a power activation signal is generated in response to a programmed alarm activation time. More specifically, the arrangement is such that each time the system power switch is turned off after the reflectance photometer system has initially been turned on, the microprocessor is programmed to determine if any of a predefined number of system alarms have been activated, prior to initiating actual power-down of the reflectance photometer system. A system alarm is considered to be activated when a user inputs a particular alarm time into the reflectance photometer system using appropriate input means.

Subsequently, the microprocessor picks out the activated alarm value which is closest to the instantaneous time when the calculation is made. The result of such a calculation is a number corresponding to the number of minutes until the time when the alarm should be activated. This number is then translated into a count value corresponding to the exact number $T_p$ of predetermined time periods, preferably 30 second time periods, remaining until the alarm needs to be activated. The duration of the time period corresponds to the time intervals at which an alarm counter is periodically incremented toward keeping track of the passage of time up to the alarm activation time. The counter is then loaded with a number that corresponds to the difference between the maximum count value of the counter and the calculated number of predefined time periods.

Subsequently, the power supply to all the reflectance photometer system, except for the alarm clock circuit itself, is turned off. The low-power alarm circuit remains active and essentially operates by incrementing the alarm counter after the passage of each time interval corresponding to the predetermined time period. This periodic incrementing of the alarm counter continues until the calculated number of predefined time periods has elapsed following the loading of the alarm counter. At that point, the maximum count value for the counter is reached and this condition is used to generate the requisite alarm signal and activate the system microprocessor and the rest of the circuitry.

According to a preferred embodiment, a 13-bit counter/shift register is used as the alarm counter means for storing and incrementing the loaded count value. The maximum count value that can be represented by such a counter is 4096. The system is based upon incrementing the alarm counter once every 30 seconds and, accordingly, the count value loaded into the alarm counter when the system ON/OFF switch is turned off under an alarm activated condition is calculated as the difference between the value 4096 and the number of 30-second counts calculated as existing between the instantaneous time and the time when the next alarm should be activated. The calculated count value is loaded into the shift register one bit at a time by using appropriate control signals from the microprocessor.

Once the shift register has been completely loaded, an alarm supply voltage is applied to the alarm circuit components. Subsequently, the microprocessor turns off the supply of power to the rest of the reflectance photometer system. The alarm circuit uses a reference oscillator signal which is preferably derived from a crystal-controlled oscillator for accuracy and is relatively low in frequency for conserving power. In a preferred embodiment, the reference oscillator frequency is 32768 Hz. The frequency reference signal is divided down to the frequency at which the alarm counter is to be incremented, which, in the preferred arrangement using 30-second counts, corresponds to a frequency of 0.033 Hz. The signal from the frequency divider is used to periodically increment the count value stored in the alarm counter and the transistor-based switch is activated when the maximum count value, i.e., 4096, of the 13-bit shift register/counter serving as the alarm counter is reached. The activation of the transistor-based switch realizes the powering-up of the rest of the circuitry at the designated alarm time.

A major advantage of the above-described alarm clock arrangement is that no special real time clock chip with a built-in alarm clock feature is required and, more importantly, there is no need for the system microprocessor itself to be periodically powered-up to determine whether or not a preset alarm time has been reached. In addition, it becomes possible to conveniently provide a plurality of alarm clock functions using a single alarm clock circuit since the microprocessor can easily be programmed to accept plural alarm times and to sequentially activate the alarm clock circuit with the requisite count value after each alarm signal is activated and the reflectance photometer system is powered down.

BRIEF DESCRIPTION OF THE DRAWINGS

Other objects and advantages of the present invention will become apparent upon reading the following detailed description and upon reference to the drawings in which.

Figure 1:
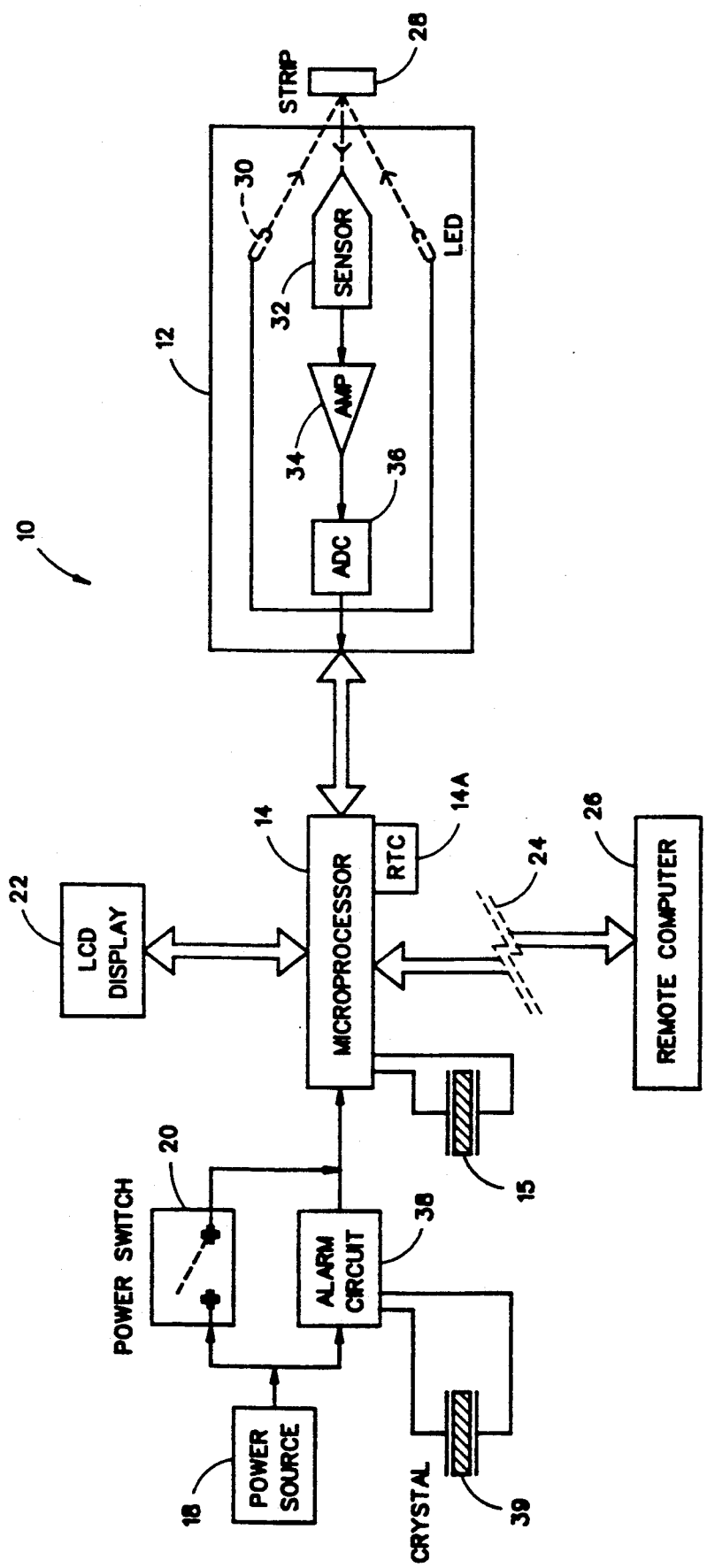
FIG. 1 is a schematic block diagram of a microprocessor-based reflectance photometer system including an alarm clock circuit according to the system of this invention.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENT

Referring now to the drawings and specifically to FIG. 1, there is shown a representative block diagram of a microprocessor-based reflectance photometer system 10 which essentially comprises a block of photometric analysis circuitry 12 operated in conjunction with a system microprocessor 14. The microprocessor 14 is cycled on the basis of a high frequency crystal 15 and is supplied with power from a power source 18, such as a battery, through a system power (ON/OFF) switch 20.

The microprocessor 14 processes the digital signals generated by the photometric sensing circuitry 12 to instantaneously generate an external indication of the blood glucose level measured by the sensing circuitry 12. Preferably, the external indication is in the form of a conventional LCD display 22. The microprocessor 14 can also be adapted to maintain a log of periodically obtained glucose level readings for use in subsequent medical analysis and treatment purposes. In this regard, the microprocessor 14 can be provided with an external interface 24 through which it may communicate the stored data to a remote computer 26.

The photometric sensing circuitry 12 is adapted to obtain optical reflectance measurements from a reagent strip 28 which has been coated with blood that has to be analyzed for glucose content. The sensing circuitry 12 essentially comprises an arrangement of light emitting diodes (LEDs) 30 which focus a narrow beam of light onto the reagent strip 28. Light reflected from the strip 28 is captured by a photosensor 32 which generates an analog signal representative of the magnitude of reflected light. The analog output of the photosensor 32 is amplified to appropriate signal levels by a linear amplifier 34. An analog-to-digital convertor (ADC) 36 is provided for converting the amplified reflectance signal into a corresponding digital value which is fed to the microprocessor 14. The signal is subsequently processed in accordance with conventional preprogrammed algorithms for generating a signal therefrom which is indicative of the glucose content of the blood with which the reagent strip 28 is coated.

In the practical operation of a reflectance photometer system of the above-described type, a user of the instrument employs some form of needle or lancet arrangement to prick himself at an accessible spot, typically the forefinger, and uses the resulting blood flow to coat a chemically-treated reagent strip provided with the instrument. In order to ensure that a minimum amount of reaction time elapses following coating of the reagent strip with the sampled blood, it is generally required that a user activate a switch on the reflectance photometer instrument panel as soon as the reagent strip is coated with blood. The switch in turn activates a preset timer which is programmed to go off after the time required for the blood to adequately react with the reagent strip has expired. When the timer does go off, the user is expected to wipe or wash the reagent strip clean of the coated blood and to position the strip in a slot provided in the reflectance photometer instrument from where the photometric sensing circuitry 12 may take the requisite reflectance readings off the strip.

The arrangement described so far is fairly conventional and the provision of any required alarm clock functions is realized in such conventional arrangements by one of the abovedescribed techniques involving either the use of a special real time clock chip 14A having some form of built-in alarm clock functions to separately generate the requisite alarm activation signals or the periodic activation or waking-up of the microprocessor to see if a programmed alarm time has in fact been reached.

In accordance with the system of this invention, one or more alarm clock functions are provided for the microprocessor-based reflectance photometer system by the provision of an alarm clock circuit 38 which is disposed between the power source or battery 18 and the microprocessor 14. The alarm circuit 38 operates on the basis of a low frequency crystal 39 and is designed to draw a negligible amount of power during its active mode of operation and essentially functions to keep track of a periodically incremented count value relative to a pre-programmed alarm time in order to generate an appropriate alarm activation signal and to cause the microprocessor 14 and the rest of the reflectance photometer circuitry to be powered up when the programmed alarm time has been reached. As a result, the reflectance photometer system need only be powered when the system is actually turned on by a user or at a programmed alarm time. During the rest of the time, the overall reflectance photometer system remains shut-off while the alarm clock circuit remains active under extremely low power conditions for realizing the requisite programmed alarm functions.

Figure 2:
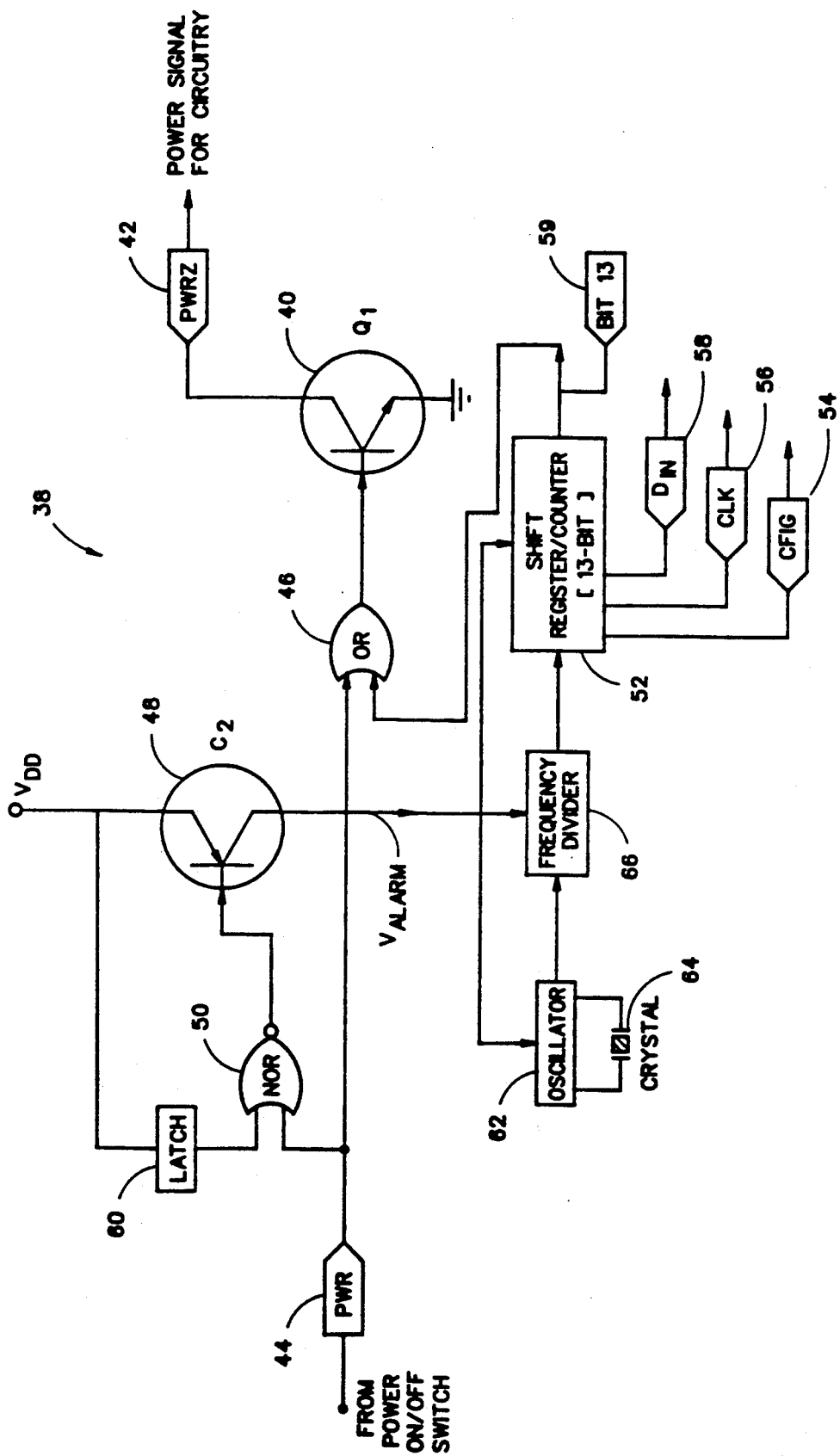
FIG. 2 is a schematic diagram of an exemplary implementation of the alarm circuit represented in FIG. 1, according to a preferred embodiment of this invention.

Turning now to FIG. 2, there is shown an illustrative arrangement of a transistor-based switch and alarm clock circuit, according to a preferred embodiment of this invention, for use as the alarm circuit 38 in the reflectance photometer system depicted in FIG. 1. As shown therein, the circuit 38 includes a NPN transistor $Q_1$ designated by the numeral 40, the output of which constitutes a power signal (PWRZ) 42 which activates or deactivates the reflectance photometer circuitry depending on whether or not the transistor Q is on or off.

The transistor $Q_1$ is activated by a power signal (PWR) 44 which is driven high when the system power switch, i.e., the ON/OFF switch, for the reflectance photometer system is turned on. The power signal 44 is in turn fed to an OR-gate 46, the output of which is linked to the base of transistor $Q_1$. The emitter of transistor $Q_1$ is grounded and, accordingly, the output of the transistor, i.e., the power signal 42, which is drawn from its collector, goes high when the power signal 44 from the ON/OFF switch goes high.

A second transistor $Q_2$, which is of the PNP type and designated by the reference numeral 48, is provided for the application of power to the basic alarm clock circuitry when the system power switch is activated. More specifically, the power signal 44 is provided as an input to a NOR-gate 50, the output of which is connected to the base of the transistor $Q_2$. The emitter of transistor $Q_2$, is provided with the alarm supply voltage $V_{dd}$ (preferably 3 volts) which is required for operation of the alarm clock circuitry. The output of transistor $Q_2$ is taken from its collector and essentially constitutes the alarm supply voltage. Accordingly, the output of NOR-gate 50 goes low anytime the power signal 44 is high and, in turn, turns transistor $Q_2$ on so that the alarm voltage is applied to the alarm clock circuitry.

The alarm clock circuitry includes a shift register/counter 52 which, as described above, has a 13-bit capacity according to a preferred embodiment. As also described above, any time the reflectance photometer system is turned off, the microprocessor calculates the count value to be loaded into the alarm counter 52 for implementing a particular alarm clock function. The calculated count value is subsequently loaded into the 13-bit shift register 52 one bit at a time by sequentially outputting a bit on the $D_{IN}$ line 58 and toggling a clock signal CLK (designated as 56) low.

The circuit arrangement is also provided with means for making the output of NOR-gate 50 go low once the loading operation is completed. More specifically, a 3-bit latch 60 is linked to the other input of NOR-gate 50 and is powered by the alarm supply voltage $V_{dd}$. The latch 60 is loaded once all 13 bits of the shift register 52 have been loaded, as indicated by the status of the 13th bit output line 59. The loading of the latch 60 causes a high signal to be fed as an input to the NOR-gate 50, whereby the output of the gate goes low which, in turn, maintains the alarm supply voltage applied to the alarm circuitry. At this point, the system microprocessor 14 is used to take the system power line 44 low which, in turn, causes the output of OR-gate 46 to go low thereby turning off the transistor $Q_1$. Consequently, the reflectance photometer activation signal 42 also goes low and shuts off all power to the reflectance photometer system.

At this stage, the reflectance photometer system is in its power-down mode whereby only the alarm clock circuit is active and draws a minimal amount of power and yet continues to monitor the programmed alarm time. More specifically, a reference oscillator 62 is used to generate a low frequency signal in conjunction with a crystal 64. The reference signal is processed by a frequency divider 66 to be down-converted to the predetermined frequency at which the shift register 52 is to be incremented. According to a preferred embodiment, as discussed above, the count value in the shift register 52 is incremented every 30 seconds and, accordingly, the frequency divider 66 is used to down-convert the frequency of the reference signal to a value of 0.033 Hz.

The count value in the shift register 52 is incremented or up-counted on the basis of the divided frequency signal generated by the frequency divider 66 and the up counting continues until the 13-bit counter counts up to its maximum count value, i.e., about 4096, whereupon the 13th bit in the counter, i.e., the overflow bit, goes high. The output line of shift register/counter 52 is connected as the other input to OR-gate 46 and functions to render the output of the gate 46 high when the 13th bit in the counter 52 goes high. This, in turn, turns on the transistor $Q_1$ and thereby causes the activation power signal 42 to go high and power up the overall reflectance photometer system.

It should be noted that the above-described alarm circuit arrangement is such that once the reflectance photometer system has been turned off, it can be turned on either by turning on the system power switch, which causes the power signal 44 to go high or by appropriately up-counting the preloaded count value in the 13-bit shift register 52. Thus, the only components that need to remain powered in order to realize the alarm function after the reflectance photometer system has been turned off are the oscillator 62, the frequency divider 66 and the shift register/counter 52. These components are extremely economical in power consumption and, accordingly, constitute a negligible power drain on the system power source or battery in the alarm mode of operation.

In experimental implementations of an alarm circuit of the type described above in connection with FIG. 2 and using standard components for implementing the alarm clock circuit, it was found that the power consumption with the alarm clock circuit being enabled was less than 5 microamps. This magnitude of current draw is negligible and has an insignificant effect on battery life. It was also determined that power consumption with the alarm function disabled using the 3-bit latch 60 (see FIG. 2) was about 0.5 microamps.

Another advantage accruing from the simple alarm clock circuit of this invention is that the two major components comprising the circuit, i.e., the 13-bit shift register/ counter 52 and the reference oscillator 62, constitute standard components which are available with conventional microprocessor circuits commonly used in conventional reflectance photometer systems. The reference oscillator 62, in particular, has a commonly used clock frequency of 32.768 KHz which can be easily down-converted by the divider 66 to the requisite level.

Also, some form of shift register/counter is a standard sub-component of ADC circuits used in the photometric sensing circuitry of reflectance photometer instruments. In utilizing such an ADC-based shift register/counter as the alarm counter for the alarm circuit of this invention, a control signal $C_{fig}$ from the microprocessor 14 is used in its high state to configure the ADC shift register/ counter as a shift register while loading the calculated count value into the register. The control signal $C_{fig}$ is subsequently taken low to activate the register/counter into a count mode for being periodically incremented on the basis of the frequency signal generated by the frequency divider.

Figure 3:
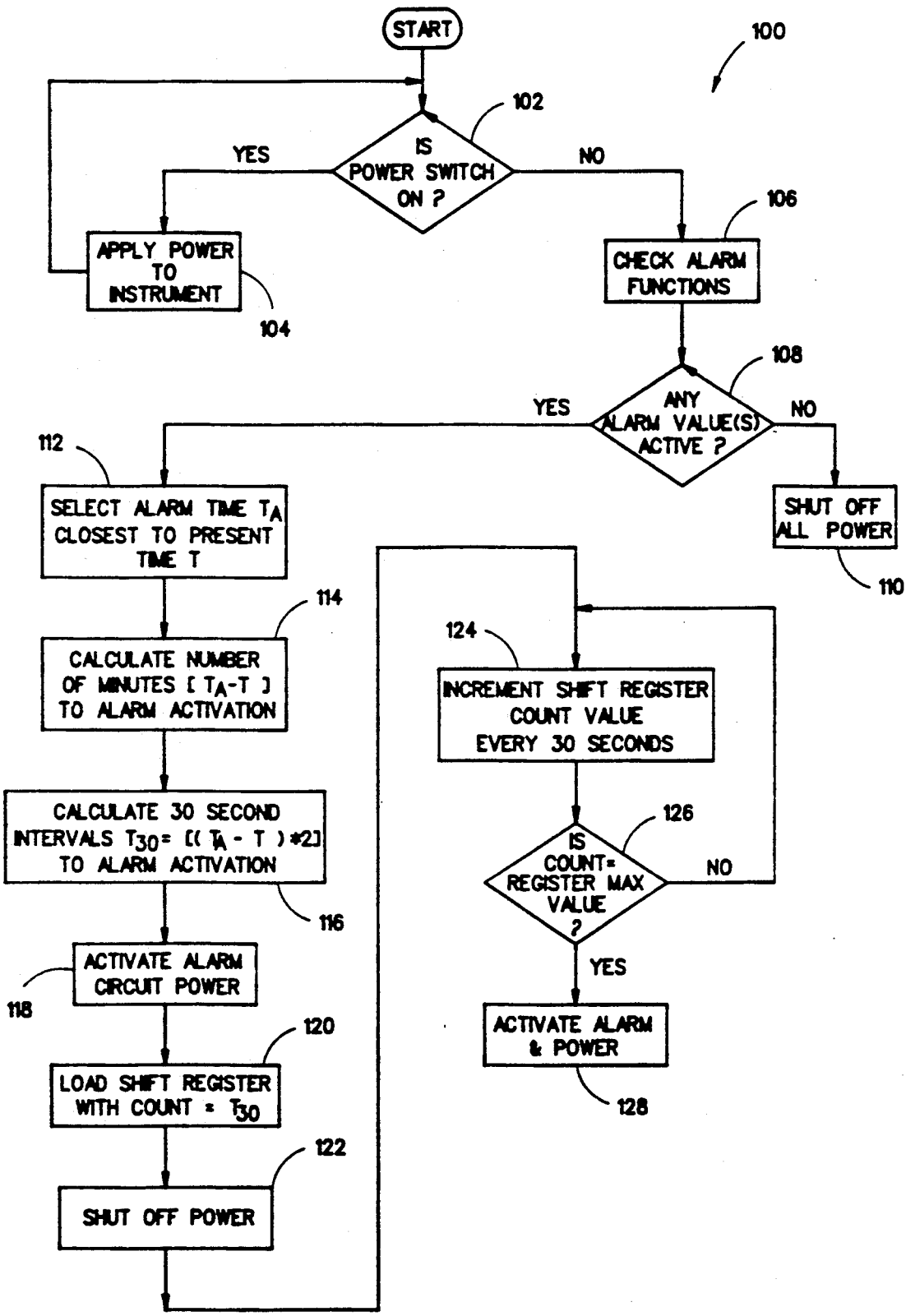
FIG. 3 is a simplified flow chart illustrating the sequence of operation of a microprocessor-based reflectance photometer system using the alarm clock circuit according to the present invention.

Referring now to FIG. 3, there is shown a flow diagram of the sequence of operation involved in utilizing the above-described alarm circuit in conjunction with a microprocessor-based reflectance photometer system. As illustrated in FIG. 3, the flow sequence 100 involves a check at step 102 to see if the system power (ON/OFF) switch is on. An affirmative answer leads to step 104 where the system power source is connected to the reflectance photometer circuitry by taking the activation signal 42 (see FIG. 2) high. If the power switch is not found to be on, i.e., the switch is off, step 106 is accessed where the microprocessor checks the plurality of alarm functions provided in the reflectance photometer system.

At step 108, a determination is made as to whether or not any alarm functions are active by virtue of having an alarm time inputted in correspondence thereto. If none of the alarm functions is found to be active, step 110 is accessed where all power to the reflectance photometer system is shut off.

If the answer at step 108 is found to be affirmative, step 112 is accessed where the microprocessor selects the alarm time $T_a$ which is closest to the instantaneous time T at the time of determination. Subsequently, at step 114, the microprocessor calculates the number of minutes remaining prior to the required alarm activation relative to the instantaneous time. This calculated number of minutes corresponds to the difference between the selected alarm time $T_a$ and the instantaneous time T.

Next, at step 116, the microprocessor calculates the number of 30 second intervals $T_{30}$ existing prior to the required alarm activation time. This quantity $T_{30}$ is calculated as being equal to twice the number of minutes calculated at step 114.

Subsequently, at step 118, the alarm circuit power is activated to ensure that the circuit is ready for implementing the up-counting operation on the shift register provided in the circuit. At step 120, the calculated count value $T_{30}$ is loaded into the shift register and, subsequently, at step 122, power to the reflectance photometer is shut off by taking the activation signal low.

The succeeding steps in FIG. 3 correspond to the manner in which the alarm circuit monitors the alarm activation time. More specifically, at step 124, the shift register/count value is incremented every 30 seconds on the basis of the down-converted frequency signal generated by the frequency divider 66 (see FIG. 2).

Next, at step 126, a check is made to see if the periodic incrementing of the shift register/count value has realized the maximum count value of the register. This is accomplished by monitoring the status of the most significant bit, i.e., bit 13 of the 13-bit shift register/counter 52. If the answer at step 126 is found to be in the negative, i.e., the maximum count value has not been reached, the system loops back to step 124. If, however, the answer at step 126 is found to be in the affirmative, it is an indication that the alarm activation time has been reached and, at step 128, the required alarm activation signal is generated and power is turned on to the reflectance photometer system.

It will be apparent from the foregoing that the present invention provides a simple, low-power and conveniently implemented alarm clock circuit which is particularly adapted for use with microprocessor-based reflectance photometer systems. The circuit implementation is inexpensive, consumes a negligible amount of power in the alarm activation mode, and totally dispenses with (i) the need for special real time clock chips with built-in alarm clock functions which require external circuitry for applying power to the rest of the system; and (ii) the periodic and power consuming activation of the system microprocessor to keep track of the instantaneous time relative to the alarm activation time. The circuit according to the present invention is particularly adapted to be implemented with the microprocessor and photometric circuitry subcomponents which are commonly used in conventional reflectance photometer systems. In particular, the programmable alarm clock system according to this invention can be used to provide multiple alarm functions in conjunction with appropriate programming of the microprocessor.

I claim:

1. An alarm clock system for generating an alarm control signal at a predefined time $T_A$ comprising:
    means for calculating a count value corresponding to the number $T_p$ of predefined time periods existing between a given instantaneous time and the predefined time $T_A$;
    means for generating a reference signal corresponding to the passage of each of said predefined time periods;
    storage means for being loaded with and for storing said count value and incrementing said stored count value each time said predefined time period has elapsed; and
    means for generating the alarm control signal when said stored count value has been incremented to a predefined maximum value.

2. The alarm clock system set forth in claim 1 wherein said storage means comprises a shift register/counter which is implemented as a shift register when said count value is being stored therein and as a counter when said stored count value is being incremented.

3. The alarm clock system of claim 1 wherein said reference signal generating means comprises a frequency source, the output of which is down-converted by divider means to a frequency corresponding to said predefined time periods.

4. In a microprocessor-based reflectance photometer system for measuring the glucose content of blood and providing an indication thereof, said system comprising photometric sensing circuitry operating in conjunction with a programmable microprocessor and associated circuitry, said sensing and microprocessor circuitry being powered by a system power source through a system power switch, the improvement comprising
    the provision of an alarm clock circuit associated with said power source and said microprocessor and sensing circuitry, said alarm circuit adapted to be activated when the reflectance photometer system is powered down by activating said power switch and an alarm activation time is input to said system, and to generate an alarm control signal for powering up said sensing circuitry and said microprocessor circuitry when said alarm activation time has been reached, said alarm clock circuit comprising:
    means for storing a count value corresponding to the number of predefined time periods to be elapsed from a given instantaneous time to reach said alarm activation time;
    means for generating a reference signal corresponding to the passage of each said predefined time period subsequent to said instantaneous time;
    means for incrementing said stored count value after the passage of each said predefined time period thereafter; and
    means for generating said alarm control signal when said stored count value has been incremented to a predefined maximum value.

5. The improved reflectance photometer system as set for in claim 4 wherein said storing means comprises a shift register/ counter which is implemented as a shift register when said count value is being stored therein and as a counter when said stored count value is being incremented.

6. The improved reflectance photometer system as set forth in claim 5 wherein said reference signal generating means comprises a reference oscillator, the output of which is down-converted by divider means to a frequency corresponding to said predefined time periods.

7. The improved reflectance photometer system as set forth in claim 6 wherein said shift register/ counter is a 13-bit register, said predefined time period is 30 seconds, and said predefined maximum value is about 4096.

8. The improved reflectance photometer system as set forth in claim 7 wherein said stored count value is calculated by said system microprocessor by (i) calculating the number of minutes existing between said instantaneous time and said alarm activation time and (ii) subsequently calculating the number of 30-second intervals existing therebetween.

9. The improved reflectance photometer system as set forth in claim 5 wherein said shift register/ counter constitutes an integral part of said sensing circuitry.

10. The improved reflectance photometer system as set forth in claim 6 wherein said reference oscillator operates at an output frequency of 32.768 KHz and said frequency divider means generates an output frequency of 0.033 Hz.

11. An alarm clock circuit for generating an alarm control signal at a predefined alarm activation time comprising:
    means for storing a count value corresponding to the number of predefined time periods to be elapsed from a given instantaneous time to reach the predefined alarm activation time;

means for generating a signal corresponding to the passage of each predefined time period subsequent to said instantaneous time;

means for incrementing said stored count value after the passage of each predefined time period thereafter; and means for generating said alarm control signal when said stored count value has been incremented to a predefined maximum value.

12. The alarm clock circuit set forth in claim 11 wherein said storing means comprises a shift register/counter which is implemented as a shift register when said count value is being stored therein and as a counter when said stored count value is being incremented.

13. The alarm clock circuit set forth in claim 12 wherein said reference signal generating means comprises a frequency source, the output of which is down-converted by divider means to a frequency corresponding to said predefined time periods.

14. The alarm clock circuit set forth in claim 13 wherein said shift register/counter is a 13-bit register, said predefined time period is 30 seconds, and said predefined value is 4096.

15. The alarm clock circuit set forth in claim 14 wherein said stored count value is determined by (i) calculating the number of minutes existing between said instantaneous time and said alarm activation time and (ii) subsequently calculating the number of 30-second intervals existing therebetween.

* * * * *